United States Patent
Bogden et al.

(10) Patent No.: US 6,195,449 B1
(45) Date of Patent: Feb. 27, 2001

(54) METHOD AND APPARATUS FOR ANALYZING DATA FILES DERIVED FROM EMISSION SPECTRA FROM FLUOROPHORE TAGGED NUCLEOTIDES

(76) Inventors: Robert Bogden, 909 E. 6th St., Moscow, ID (US) 83843; Marcel De Leeuw, Appt. 102-264, rue Sonja Henie, 34090 Montpellier (FR)

( * ) Notice: Subject to any disclaimer, the term of this patent is extended or adjusted under 35 U.S.C. 154(b) by 0 days.

(21) Appl. No.: 08/858,102

(22) Filed: May 18, 1997

(51) Int. Cl.[7] .................................................. G06K 9/00
(52) U.S. Cl. ............................................ 382/129; 382/190
(58) Field of Search ..................................... 382/190, 128, 382/129, 191, 134, 133, 192, 201, 206; 436/56, 94, 172; 702/19, 20

(56) References Cited

U.S. PATENT DOCUMENTS

| | | | |
|---|---|---|---|
| 4,482,966 | * 11/1984 | Mito et al. ............................ | 364/498 |
| 5,614,386 | * 3/1997 | Metzker et al. ..................... | 435/91.1 |
| 5,667,971 | * 9/1997 | Hochberg ............................. | 435/6 |
| 5,729,694 | * 3/1998 | Holzrichter et al. ................ | 395/2.17 |

* cited by examiner

Primary Examiner—Bhavesh Mehta
Assistant Examiner—Kanji Patel
(74) Attorney, Agent, or Firm—Mallinckrodt & Mallinckrodt; Robert R. Mallinckrodt; Peter M. Peer

(57) ABSTRACT

An automated method and apparatus is provided for the analyzing of data files derived from fluorophore emissions detected during observation of fluorophore labeled nucleotide polymers such as is done during the sequencing of bases in nucleotide polymers. The analysis steps of the method depend upon a key step of quantifying features of the emission peaks whereby subsequent steps as base calling can be performed and whereby individual emission spectra within the data files of two or more samples can be automatically synchronized, compared, and differences detected and signaled. The quantified peak information provides for the use of fuzzy logic and the assignment of truth values or scores to be assigned to the base calls. optimally, individual peaks within the data file are corrected by distortions, the peaks enhanced, and the overall data file information augmented to further improve the accuracy of the analysis of the data and reduce manual labor requirements.

14 Claims, 11 Drawing Sheets

Figure 1:
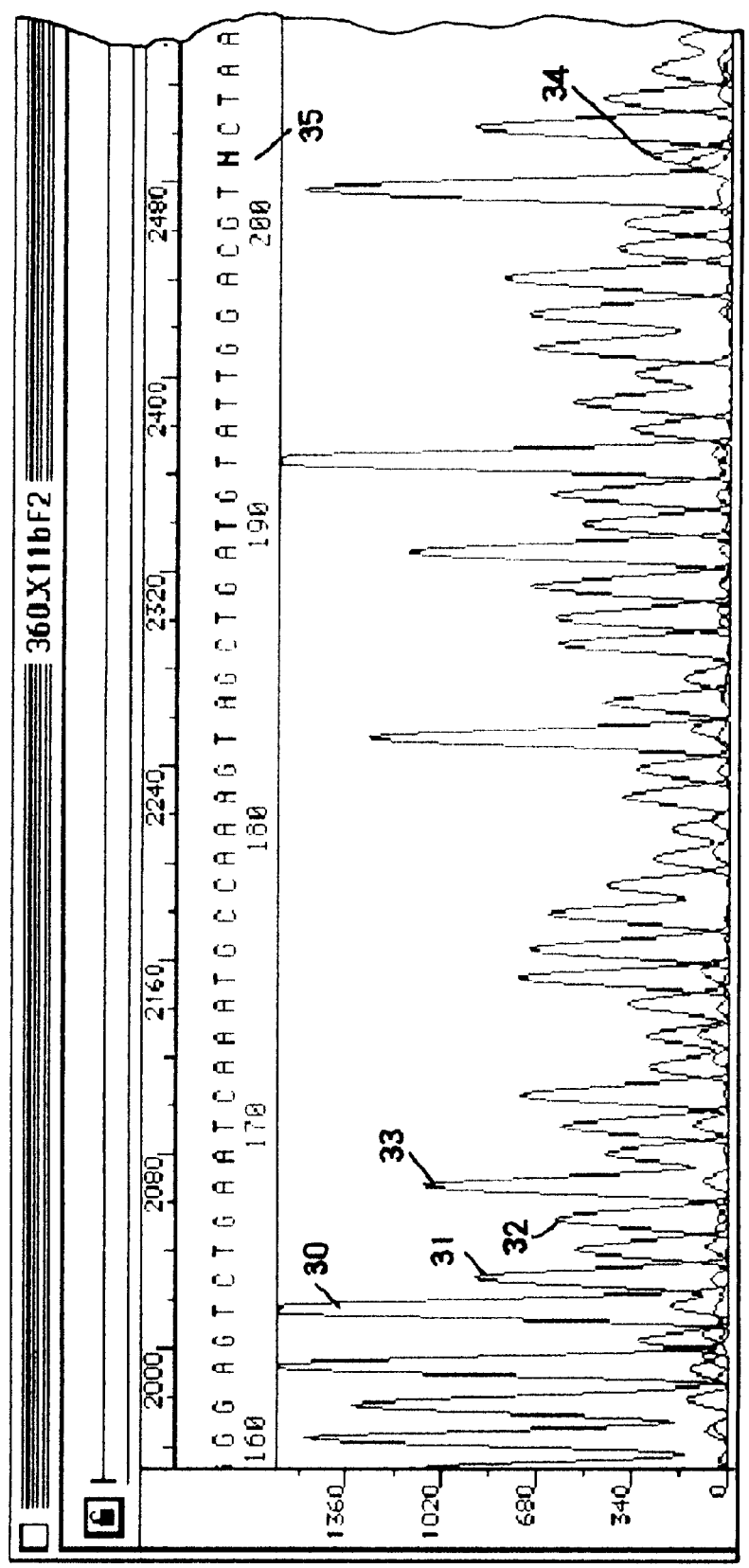

Peak Detection & Feature Extraction Detail
(Speech recognition equivalent provided)

The chromatogram signals are corrected for certain distortions: peak clipping and contextual influence. (Equivalent to noise removal in speech recognition)

↓

Prior to peak detection, the peak shape can optionally be enhanced, using the $2^{nd}$ time domain derivative of the chromatogram signals, in order to improve peak separation. (This has no equivalent in speech recognition)

↓

Peaks are detected on the corrected chromatogram signals. (Equivalent to phoneme or phone segmentation in speech recognition)

↓

For each detected peak a feature vector is extracted; quantifying peak spacing, peak height and peak shape. A two fold identification of the peak is made of the best and the second best base call candidates. (Equivalent to calculating MFCC spectral features and signal energy, except the scope is only the segmented phone, not a fixed 10ms analysis as used for HMMs)

↓

Peaks are inserted and deleted from the sequence, in order to satisfy peak spacing continuity criteria, ruled by local estimations of the average peak spacing. (Equivalent to phoneme insertion/removal based on phoneme duration criteria and local speech rate estimations)

FIG. 6

Synchronization Detail
(Speech recognition equivalent provided)

In comparing peaks from sample and reference, a fuzzy logic truth value or score is calculated from the extracted features.

↓

For each sample/reference pair, the gross mapping function is recalculated, using subsets of 10 peaks, and using the extracted features. The original base call is not used anymore.

↓

The gross alignment is used as a seeding of the fine alignment, which consists of mapping each possible peak triplet from sample to reference. (Equivalent to triphones used in HMMs in speech recognition). The fuzzy logic score makes such alignment possible in regions of the sequence where a classical base call comparison would not be able to generate a correct alignment.

↓

Peak pairs are selected from the fine alignment, which have yielded a sufficient score and a chromatogram mapping function is calculated from those pairs. (Equivalent to speech recognition mapping function calculating using the dynamic time warping (DTW) algorithm

↓

The mapping function is filtered in order to exclude possible discontinuities. Such filtering is allowed because the gel migration speed is locally constant.

↓

The sample chromatogram is recalculated using the mapping function. Because gel migration speed is locally constant, the mapping function can be interpolated in order to find the equivalent data point in the sample chromatogram for each data point in the reference chromatogram.

FIG. 8

Signal Difference & Polymorphism Detection Detail

Any signal difference between sample and reference is considered a potential polymorphic locus, without confining the analysis to ASCII text base calls.

↓

Heterozygote changes are detected by a decrease in signal intensity of one base and the presence of signal in a different base.

↓

Homozygous changes are detected by the absence of signal in predicted base and presence of signal in a different base.

↓

Small insertions and deletions are detected after the chromatogram contains superimposed data from both alleles. The resulting frameshift is not mistaken for miscalled N bases.

↓

| There is a user adjustable sensitivity scale providing control of the level of signal difference required to flag a mutation | ← → | There is a "subtraction switch" allowing users to remove all signal information contained in both sample and reference, providing the user with a fast visual information at any locus. |

↓

Results from the forward and reverse chromatograms are compared, eliminating any artifacts found in only one direction

FIG. 9

METHOD AND APPARATUS FOR ANALYZING DATA FILES DERIVED FROM EMISSION SPECTRA FROM FLUOROPHORE TAGGED NUCLEOTIDES

BACKGROUND OF THE INVENTION

1. Field

The present invention relates generally to the field of nucleotide investigations, and more particularly to the detection and analysis of emission spectra generated during observation of excited fluorphore labelled nucleotide polymers undergoing separation by size, such as is done during the sequencing of bases in nucleotide polymers.

2. State of the Art

The genetic material of higher organisms comprises two strands of DNA. Each DNA strand is a polymer of nucleotide monomers and each monomer consists of a sugar residue (deoxyribose), a phosphate residue, and a purine or pyrimidine base. The monomers are linked in a continuous chain by a phosphoribosyl backbone. The double stranded DNA prefers a helical orientation and exists as a long linear strand in higher organisms (up to several centimeters in length in man) with its phosphoribosyl backbone oriented outwardly of the helix and the sequentially ordered bases oriented inwardly along the axis of the helix whereby complementary hydrogen bonding between bases hold the two strands together. By complementary it is understood that adenine nearly always forms hydrogen bonds with thymine and cytidine with guanidine. The phosphoribosyl backbone has a free hydroxyl group at the 3' position extending from the terminal deoxyribose residue at one end and a free terminal phosphate group attached at the 5' position of its last deoxyribose residue at the other, thus giving a directional orientation to the opposing strands.

It is the sequence of the four bases found on the strands of DNA, (denoted A, G, T, and C), that is the genetic code directing the synthesis of all the polypeptides or proteins (enzymes, collagen, muscle, etc. synthesized as a linear sequence of amino acid monomers). These polypeptides perform the metabolic processes essential to life and health and provide structure and mobility to organisms. The code is based on a sequence of three bases, thus $4^3$ or 64 "code words" exist in the code. One triplet code is a start command, directing the initiation of synthesis of amino acid polymers (polypeptides), most triplets code for a particular amino acid to be added to the linear polypeptide chain, and a few triplet codes are stop commands directing the termination of synthesis of the polypeptide. A gene consists of the series of triplet codes, that is, the DNA sequence which directs the synthesis of a single protein. One gene codes for one protein. The industrial and research community desire to learn the sequence of DNA in all genes in humans and some other organisms and thereby harness this genetic code for a variety of useful purposes. With over $3\times10^9$ bases making up the genes in humans, the enormity of the task of determining their sequence as they occur in the genes is readily appreciated.

While the above discussion has used the term DNA and referred to DNA sequencing, and uses the terms DNA and DNA sequencing hereinbelow, it is understood that the invention has application to sequencing methods of any nucleotide polymer, e.g., amplified microsatellite nucleotide polymers and other methods involving the use of fluorescently tagged nucleotide polymer fragments used to generate a chromatogram.

Two methods of sequencing form the basis for large scale sequencing operations, a so-called chemical method and an enzymatic method. The enzymatic method exploits the process of DNA replication which always occurs in the 5' to 3' direction by the addition of a new nucleotide to the 3' terminus of the growing DNA polymer catalyzed by an enzyme, DNA polymerase. The process is known as primer extension and the method of sequencing upon which it is based is the enzymatic or dideoxy method of DNA sequencing. Sanger et al., *Proc. Natl. Acad. Sci.*, U.S.A. 74, 5463–5467 (1977). The chemical method of DNA sequencing was developed by A. M. Maxam and W. Gilbert, and is described in *Proc. Natl. Acad. Sci.*, Vol. 74, p. 560 (1977). Each method is well known and well described in the references cited above and are equally applicable to the invention. Suffice it to say, they involve a number of steps and result in fragments of DNA of varying sizes that end with a different base (A, T, C, or G). The determination of DNA sequence in these methods depends on separating the DNA fragments produced by order of size and either by what base they contain (when each lane has only one reaction product) or by what fluorophore tag is detected if all four reaction products are in one lane as in commercially popular sequencing machines. If the shortest fragment ends in A, then the first base in the sequence is A. If the next longest fragment ends in T, then the next base in the DNA sequence is T and so on. This is the basic algorithm for "base calling", i.e., determining the sequence of purine and pyrimidine bases in a strand of DNA.

One commercially popular automatic sequencer, the ABI 373A®, available from Applied Biosystems, Inc., Foster City, Calif., performs the following steps after a nucleotide polymer is sampled and reaction products of varying length obtained. The reaction product fragments are tagged with a fluorophore, resolved by size by inducing them to migrate through a polyacrylamide gel via an electrical charge across the gel (gel-electrophoresis), exposed to an electromagnetic wave source to induce the emission of electromagnetic energy (fluorescence by the tag), and the emitted energy detected by a detector to produce an analog signal. The analog signal is sampled and the sampled values transmitted to a data file referred to as a gel file. The gel file data is then "tracked" and processed by ABI Sequencer® analyzer software which generates chromatogram data and stores it in a chromatogram data file. The software then automatically determines the DNA base sequence from the chromatogram data and stores the sequence data as part of the chromatogram data file. Examples of patented automatic sequencing apparatus and methods include U.S. Pat. No. 4,811,218 to Hunkapiller et al. issued Mar. 7, 1989 assigned to Applied Biosystems, Inc. (ABI), and U.S. Pat. No. 5,556,790 to Pettit issued Sep. 17, 1996, the disclosures of which are incorporated herein by reference. These methods and such commercially available instruments as the ABI 373A® as discussed and the Pharmacia A.L.F.®, from Pharmacia, Inc. of Piscataway, N.J., and the Licor® Sequencer from Licor of Lincoln, Nebr. all produce a chromatogram data file from an analog signal in a manner compatible with the initial steps of the present invention. It is understood that should newer methods of creating chromatogram data files be produced, they too would be compatible with the invention. In addition to the instruments and methods discussed above, other methods employing capillary electrophoresis can be used to produce a data file compatible with the initial steps of the invention. The initial steps of producing reaction products is the same, however, a gel is not used during the fragment separation step and, at least in one commercially popular machine, a CCD camera is used to detect fluorophore emission spectra. Other prior art methods not necessarily directed to gene sequencing, such as microsatellite amplification, employ fluorophore labeled nucleotides and generate signals that can be converted into chromatogram data files as well. These and yet to be developed methods which produce a signal that can be converted into a digital data file such as a chromatogram data file are compatible with the initial steps of the invention.

Some current commercial automated sequencers utilize a single gel plate which can accommodate up to 64 migration lanes simultaneously, that is, 64 unique DNA samples. The multiple lanes are generally run through the detector and detected simultaneously to increase the throughput of the sequencer. A single run on such a gel can result in collection of between 4000 and 9000 data points (one each 6 seconds) for each sample by means of intermittent sampling of the raw data generated by the detector for a gel plate run and saving the collected data generated in a gel file. This process requires between 4 and 12 hours depending on the size of the longest DNA fragments under analysis, and, consequently, the migration time which lengthens with the length of the fragment. As indicated above, the gel file data is interpreted by software and the interpreted data then stored in a so-called chromatogram data file. A chromatogram could be plotted out on paper or on a computer screen if desired.

The existing "base calling" process in automated sequencers consists of determining the DNA base sequence from the chromatogram data without the necessity of plotted graphs, except when the data is too ambiguous. Then plotted graphs must be resorted to. One of the most labor intensive and highly skilled tasks during DNA sequencing projects is viewing the original trace descriptions of the gels and resolving conflicting readings. J. Bonfield and R. Staden, *The application of numerical estimates of base calling accuracy to DNA sequencing projects, Nucleic Acid Research,* Vol. 23, No. 8, pp. 1406–1410, 1995.

Ambiguities result and limitations are imposed upon the length of DNA strands which can be sequenced by factors inherent in current methods of tagging DNA, variations inherent in gel electrophoresis, inherent inconsistencies in the make up of the sample such as heterozygosity and other polymorphisms, and current methods of base calling including especially the available software for base calling. All these variables can result in ambiguous information such that accurate base calling is interfered with. In general, it is an object of the invention to provide a means for resolving ambiguities due to the above factors. It is a further object to identify mutated genes, homozygous and heterozygous loci within exons, introns, or, nucleotide polymers, in general, and other polymorphic anomalies from chromatographic data.

First, a closer examination of one particularly important problem that has had no satisfactory solution to date, i.e., the problem arising during gel electrophoresis. During the process of running the gel, a number of stochastic phenomena occur to change the migration speed of the DNA primer extensions within a lane and from lane to lane and cause the data collected to be nonsynchronous among the lanes. Contributing factors to nonsynchronicity include: microscopic holes in the gel matrix as a result of rate of polymerization and quality of acrylamide, break down of the polyacrylamide matrix during running, changes in migration speeds due to electrical idiosyncrasies, temperature variability throughout the gel, and variability in salt concentrations in the running buffer. All these factors combine to have an overall effect of stretching or compressing the migration speed of each sample (and the x axis of the chromatogram). The result is that two identical DNA samples, run on the same gel, in different lanes will have different electropherogram data. The effect is even more dramatic when the samples are run on different gels or on different machines. It is an object of the invention to provide means for correcting for nonsynchronicity among the lanes of one run on one instrument, among different runs, and among runs performed on different instruments.

Currently, the most expeditious way to detect differences between experimental samples and a reference is by comparing the text data, e.g., A-C-G-T-T-G-G-, for the two samples using one of the several programs available. All these prior art software programs are based on the comparison of the text strings, e.g., AC-G-T-T-G-G-. The text strings are generated by the Applied Biosystems, Inc. basecaller software when generating the chromatogram data. Such software makes base determinations by considering peak height and peak spacing. It does not consider peak size, area under the peak, presence of different colored peaks (peaks at different electromagnetic wavelengths occurring at the same migration time), peaks that are out of synchronization, or time factors involved in evolution of the peak, or quantify these variables for consideration in the base calling algorithm. In other words, there is a lack of software for analyzing and quantifying more than two of the many variables and chromatogram characteristics contained within a chromatogram data file. It is an object of the invention to consider various aspects of the chromatogram data for base calling and for detecting differences between experimental samples.

Problems with the currently available base calling algorithms arise when ambiguous data results as a consequence of so-called "contextual influences" resulting from current sequencing methods and perhaps polymerases employed in such methods. L. T. Parker et al., *Peak Height Variations in Automated Sequencing of PCR Products Using Tag Dye-Terminator Chemistry, BioTechniques,* Vol. 29, No. 1, pp. 116–121. For example, the signal emitted by the fluorophore attached to G., i.e., the G peak, following an A peak, can be weak and is, perhaps the most noticeable contextual influence. However, the G peak following C and T is also weaker. The peaks for A or T fluorescence is very strong when following a G. Such "contextual influences" or ambiguities can be resolved by sequencing the opposite direction across the problematic region, because the same problem will not be observed on the chromatogram of the primer extension reaction product using the reverse complement of the ambiguous template. For example, if the template sequence is 5'-AG-A-G-T-G-C-T-C-3', the first two G peaks might be ambiguous and difficult to call because they will follow A peaks, but the peak following the T residue may be clear. However, in the reverse complement of the template strand, the sequence is 5'-G-A-G-C-A-CT-C-T-3', the C-T-C-T portion representing the reverse complement to the A-G-A-G portion of the template. The chromatogram will show an unambiguous C peak followed by a T peak followed by another C peak followed by another T peak, so none of the ambiguities present in the target template are present in the reverse complement of the problematic region.

With a heterozygous polymorphism or other polymorphism, there is a variation in base sequence between a sample and a reference at a particular locus, i.e., one base may appear on one allele, but a random, different base will occur on the other allele, and/or the base on the otherwise complementary strand will not be the usual complementary base pair at the same locus. Such polymorphism will look exactly like an ambiguous base call in both forward and reverse sequencing reactions. Polymorphisms occur not only within exons, but within introns as well, and, therefore, the problem arising with sequencing polymorphic samples applies equally to both. Heretofore, there has been no commercially practical, simple means for determining whether an ambiguous base is a heterozygous polymorphism or artifact. Automated methods have compared only text strings which can point out differences but not resolve ambiguities that underlie the differences. Manual inspection of chromatograms can resolve questions, but is difficult and labor intensive. Hence, there has been no practical method to fully compare chromatogram data from two or more data files. It is an object of the invention to provide a method and apparatus for importing digital data files derived from signals generated during nucleotide sequencing of two or more samples, such as chromatograms from a reference person or group and a chromatogram from a potential carrier of a mutation, and to compare two or more chromatograms and distinguish between ambiguous peaks and true heterozygous polymorphisms and/or other polymorphisms, i.e., where a peak corresponding to one base is found in one chromatogram and the corresponding peak in the comparison chromatogram is for an unambiguously different base.

Much work has been done in the area of automatic speech recognition and computerized speech processing. Various approaches to analyzing speech signals have been developed and are in use to allow computers to analyze and compare digital data representative of analog speech signals. Information on speech processing is contained in the book *Neural Networks and Speech Process*, David P. Morgan and Christopher L. Scofield, Kluwer Academic Publishers (1991), and such information is incorporated herein by reference.

SUMMARY OF THE INVENTION

The inventors have discovered that many of the techniques used in processing speech signals for automatic speech recognition can be applied to analyzing chromatogram data. The above stated objects and other objects of the invention are accomplished by an apparatus and method for, in short, obtaining digital data files containing information representative of the fluorophore emission spectra generated during observation of fluorophore labeled nucleotide polymers undergoing separation by size, such as is done during the sequencing of bases in nucleotide polymers, importing one or more such data files into the memory of a digital computer device, and extracting a vector from one or more, and optimally five, peak features for each chromatographic peak, i.e., the vector quantifies such peak characteristics as peak spacing, height, area under the peak, time for evolution and devolution of the peak, and, if present, the occurrence of a secondary peak at the same location as a primary peak.

It is this quantification of peak parameters that enables automated filtration and "correcting" or "cleaning up" and "enhancement" of the peak information and better base calling. The vector extracted from the peak features, especially when derived from corrected and enhanced peaks, permit better peak detection, alignment of sample peaks with reference peaks in chromatogram data that could not otherwise be easily aligned, quantifiable comparison of corresponding peaks between two or more chromatogram data files, the detection and signaling of differences between two or more data files, and the automated determination of whether a detected difference is an artifact or a true polymorphism.

It is the comparison analysis that is perhaps the presently contemplated most useful application of the invention. In brief, two or more data files are imported into a batch file. At least one of the imported data files has been predetermined by the user to be a reference and the program provides the user the ability to select which among the imported files will be the reference. A feasibility verification first step is performed by comparing ASCII text files of initial base calls to verify sufficient correlation in the base sequences of the sample and the reference to permit at least gross alignment of the two files. The Peak Detection and Vector Extraction step discussed above is the second step of a comparision analysis. The third step is a recalculating of the gross alignment using the feature vectors instead of the ASCII base calls. The fourth step is a fine alignment or "Synchronization" step which utilizes the recalculated "gross alignment" established in the Feasibility step as a take off point for further fine alignment of the peaks of the sample and reference chromatograms that takes place in the Syncronization step. The final step is a Difference Detection and Filtering step where differences between the peaks of the finely aligned chromatograms of a sample and reference are flagged.

Correction comprises revision of the data to minimize certain distortions such as peak clipping and contextual influence such as the G following A phenomenon. Enhancement is accomplished by calculating the second time domain derivative of the chromatogram signals and using that derivative to improve peak separation. Peaks can then be better detected after which extraction of an enhanced feature vector can be obtained. A tentative labeling of the peak is then made based on the feature vector and the usual base calling algorithm (migration time, fluorophore detected), but with quantifiable peak parameters. This tentative labeling can be two fold, labeling the best and the second best base call candidates and assigning truth values or scores to the call. A binary yes or no decision that a base is present is thereby avoided. Peaks can then be inserted and deleted from the sequence in order to satisfy peak spacing continuity criteria ruled by local estimations of the average peak spacing in order to enable better synchronization, i.e., alignment, of the corrected and enhanced chromatogram with a reference.

All the analysis, correction, enhancement, and so forth takes place in a digital computer device which is preferably configured not only with the analytical software, but with user friendly interactive interfaces. The preferred software supports a variety of platforms (IBM®, Macintosh®, and Unix® and provides the user with a number of pull down menus, point and click actuators, and click and drag actuators. Among those options that may be provided are: allow the user to designate a data file as a "sample" data file or as a "reference" data file to which one or more sample files are compared; allow the user to select a single (forward) chromatogram data file for automatic analysis which, ideally, includes peak correction, enhancement, feature extraction, base calling, and assignment of truth values or scores, or to select one or many files for inclusion in a batch file; deselect files from a batch; run analysis on a batch; abort a run; and/or view the results of a run. Preferably, the interface provides the user the ability to select data files from both forward and reverse runs, and/or multiple data files for comparison analysis with a user selected reference data file. An unlimited number of batches can be processed with the number of samples limited only by hard drive storage capacity, which of course can be expanded as necessary by the user.

If the user selects two or more files for analysis and comparison, the software program automatically performs the series of corrections, enhancements, and analyses. The first analysis is a "Feasibility Verification" step in which the ASCII text files can be obtained from prior art sequencing machines or from base calls obtained by processing the chromatogram or similar data files with the software of the invention, making calls based upon extracted peak features, and creating an ASCII text file of the calls. Feasibility Verification denotes that gross alignment of the base sequences is possible. If gross alignment is possible for all samples selected, then the feasibility of processing the batch is verified and comparison analysis proceeds. Otherwise, the inability to grossly align a sample with a reference is signaled to the user and the analysis for that sample within the batch is aborted. Data files incapable of gross alignment can be removed from the batch file by the user.

The second analysis is a Peak Detection and Feature Extraction step. As mentioned, this is a key feature of the invention and has already been briefly described.

The third analysis is a Synchronization step. This is superficially similar to the initial feasibility verification step and includes another gross alignment step except that the comparison between sample and reference is based on the sequential series of vectors extracted from sequentially ordered the peak rather than sequential base calls. Synchronization is comprised of the ordered steps of: gross alignment based on the vector formed from the peak features; fine alignment; calculation of a chromatogram mapping function; and filtering of the mapping function to exclude possible discontinuities in the base sequence of the sample.

The key to the ability of the method to detect mutations and polymorphisms is a signal difference detection step, the fourth analysis step, where any signal difference in the vectors of two peaks between sample and reference is flagged and reported to the user. It is of particular note that vector differences are detected and quantified and that the analysis is not confined to ASCII text of the base calls, except in the case of comparisons between forward and reverse sequences, therefore a miscalled base will not interfere with an accurate polymorphism detection. The invention offers the further improvement over prior art methods of detecting differences between a sample and a reference in its interactive analysis interface.

This interface provides the user with the capability of selecting from among such options as: (a) adjusting the sensitivity of what will be flagged as a difference between sample and reference; (b) whether chromatograms will be viewed synchronized or unsynchronized; (c) whether chromatograms are viewed after subtraction of all similarities showing only differences; (d) whether an analysis picture is exported; (e) whether to save the sample name, reference used for comparison, the sensitivity setting used during comparison, the location of flagged differences detected at the sensitivity setting employed, and the date and time in a new text file; and (f) whether to save the ASCII text string of the bases called by the invention inside the original imported data file. The new base calls will not replace the original bases called by any initial base caller program such as that supplied by automated sequencing machine manufacturers which normally set aside a location for saving new base calls.

THE DRAWINGS

Figure 2:
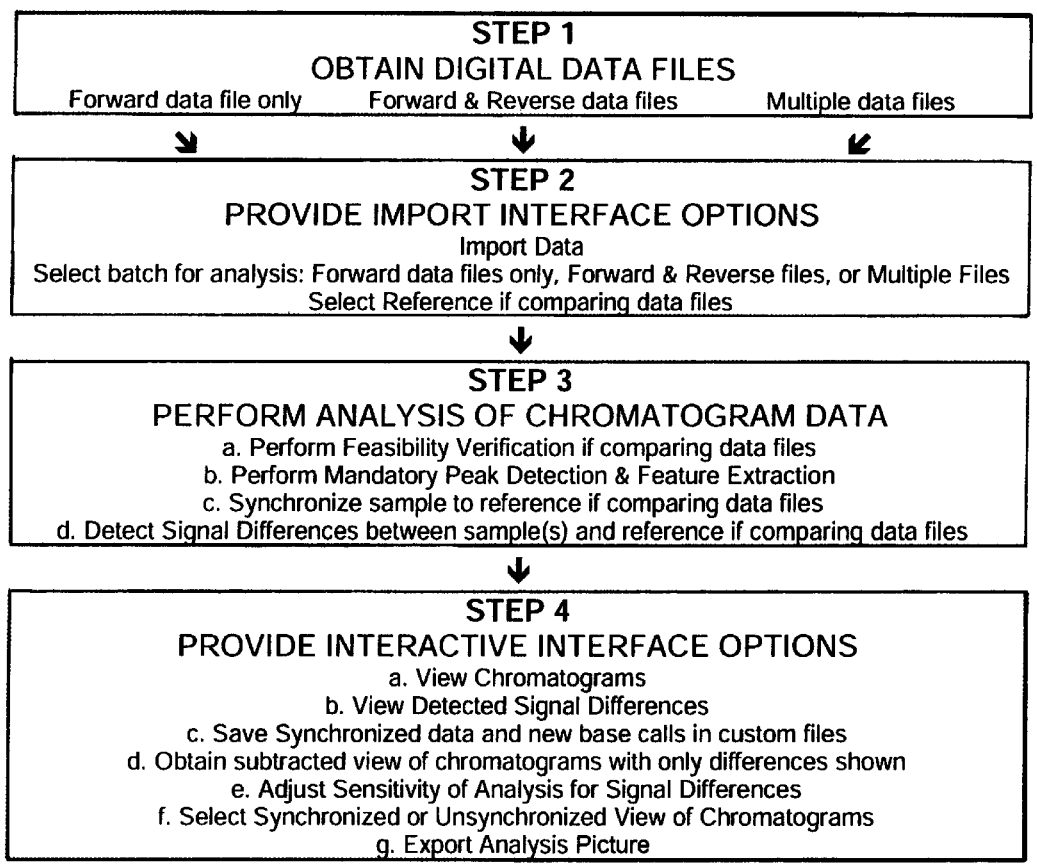
Figure 3:
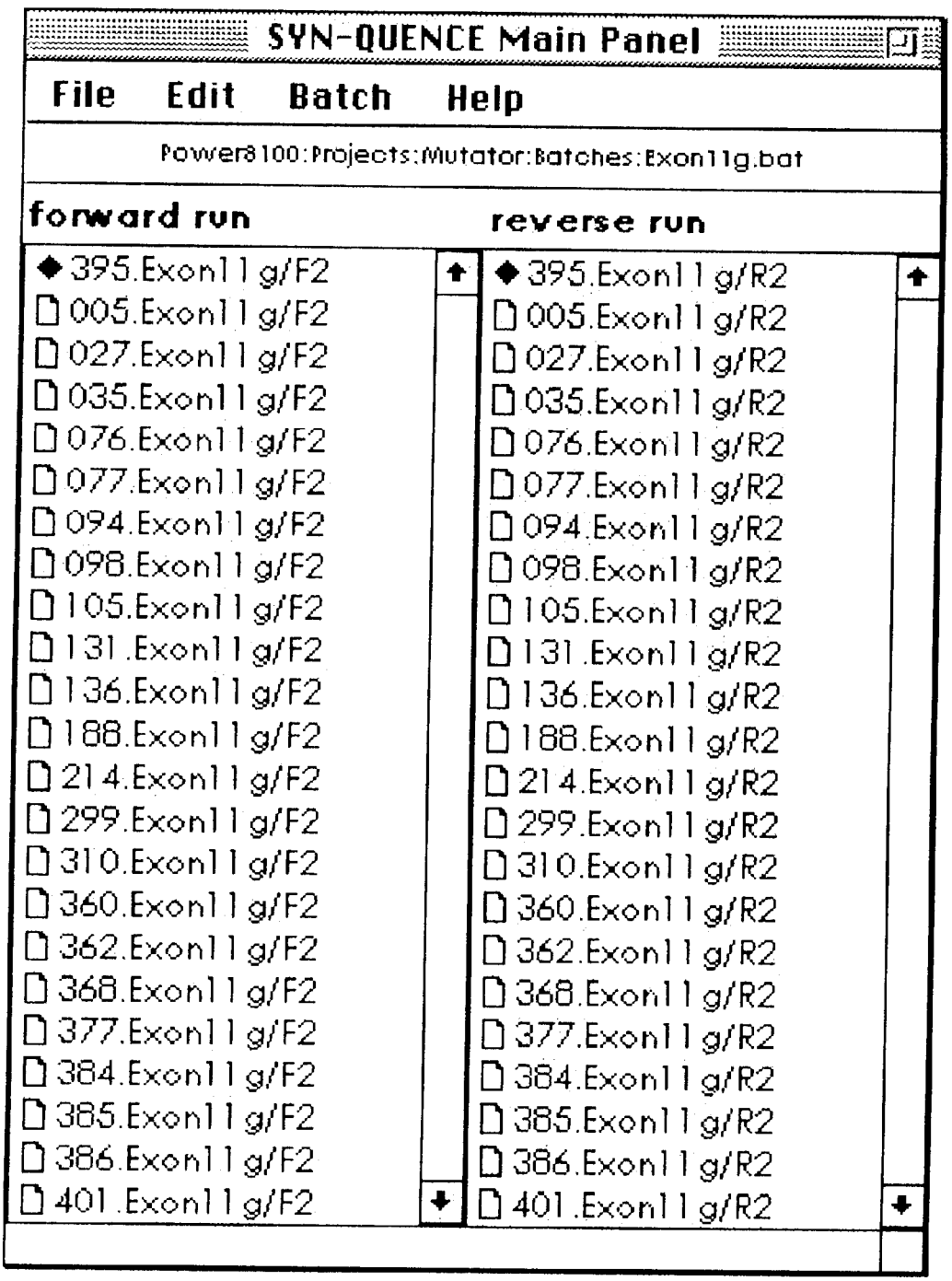
Figure 4:
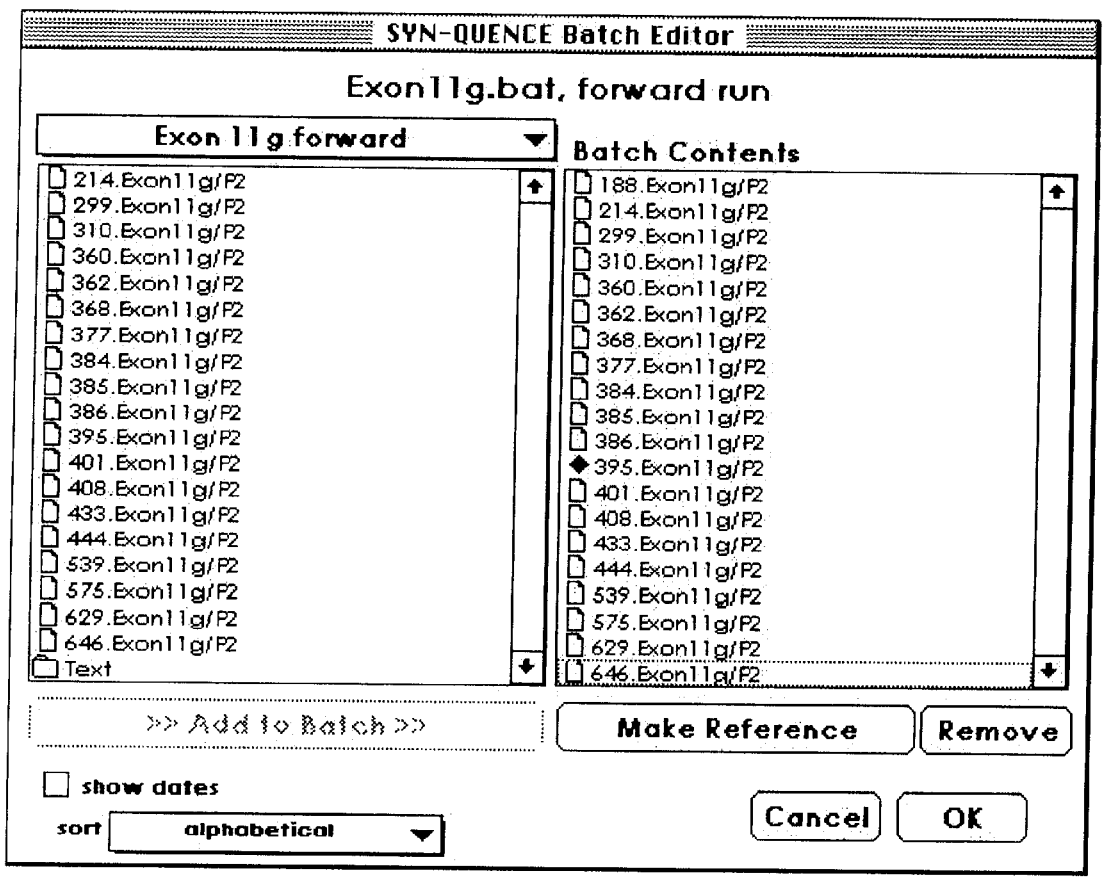
Figure 5:
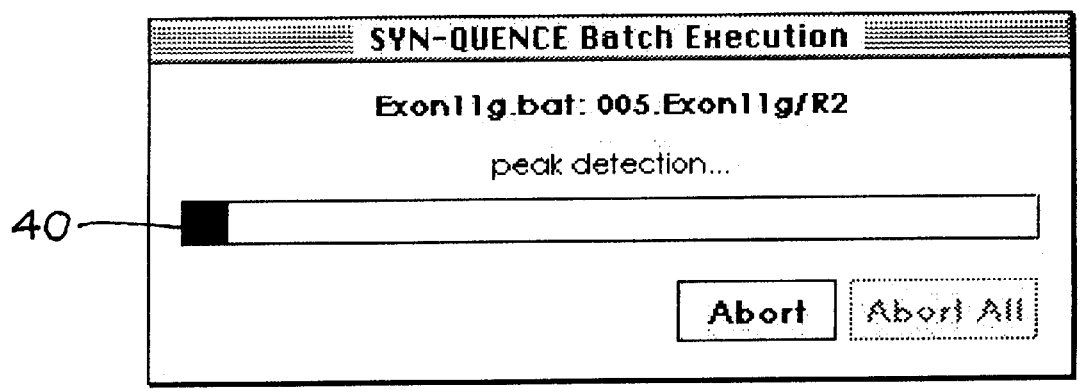
Figure 7:
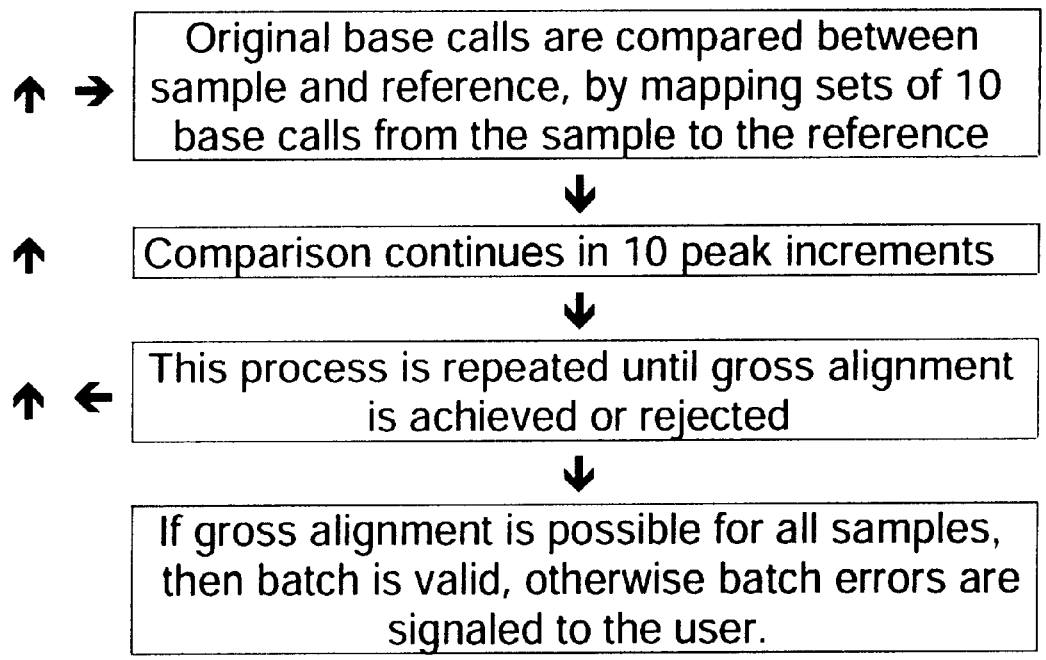
Figure 10:
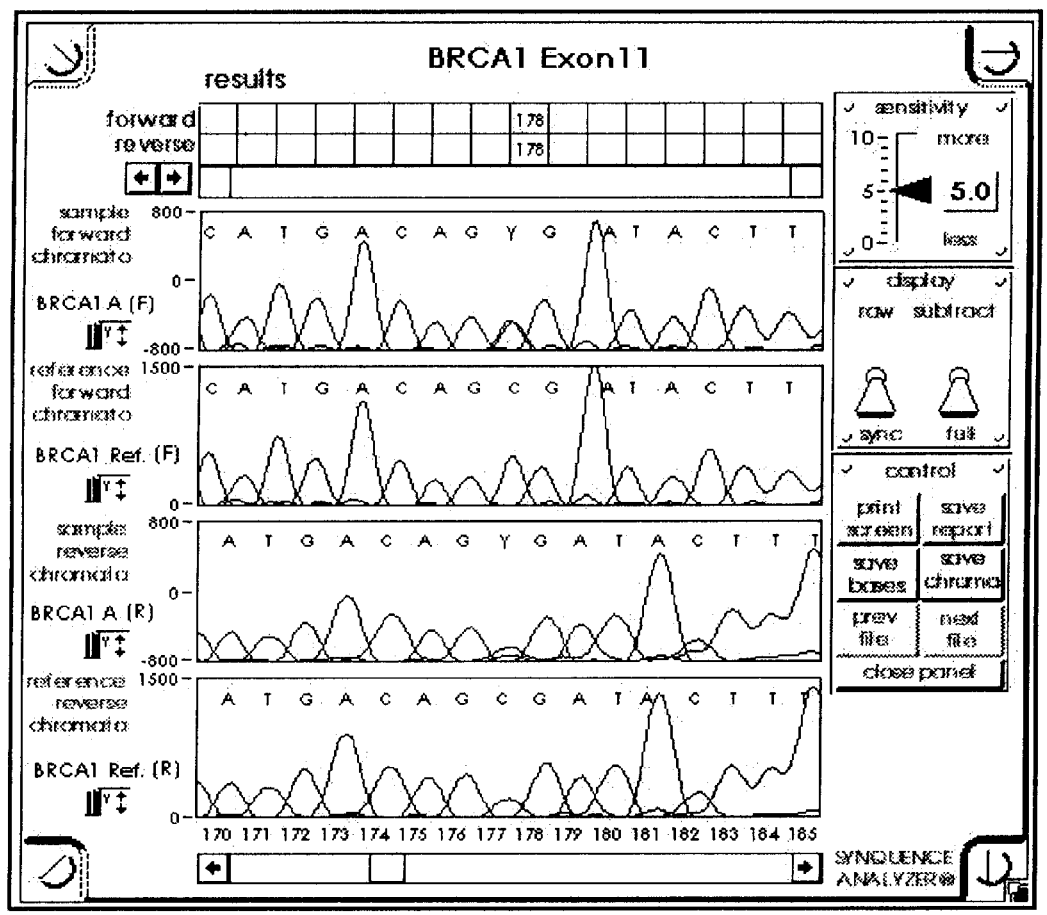
Figure 11:
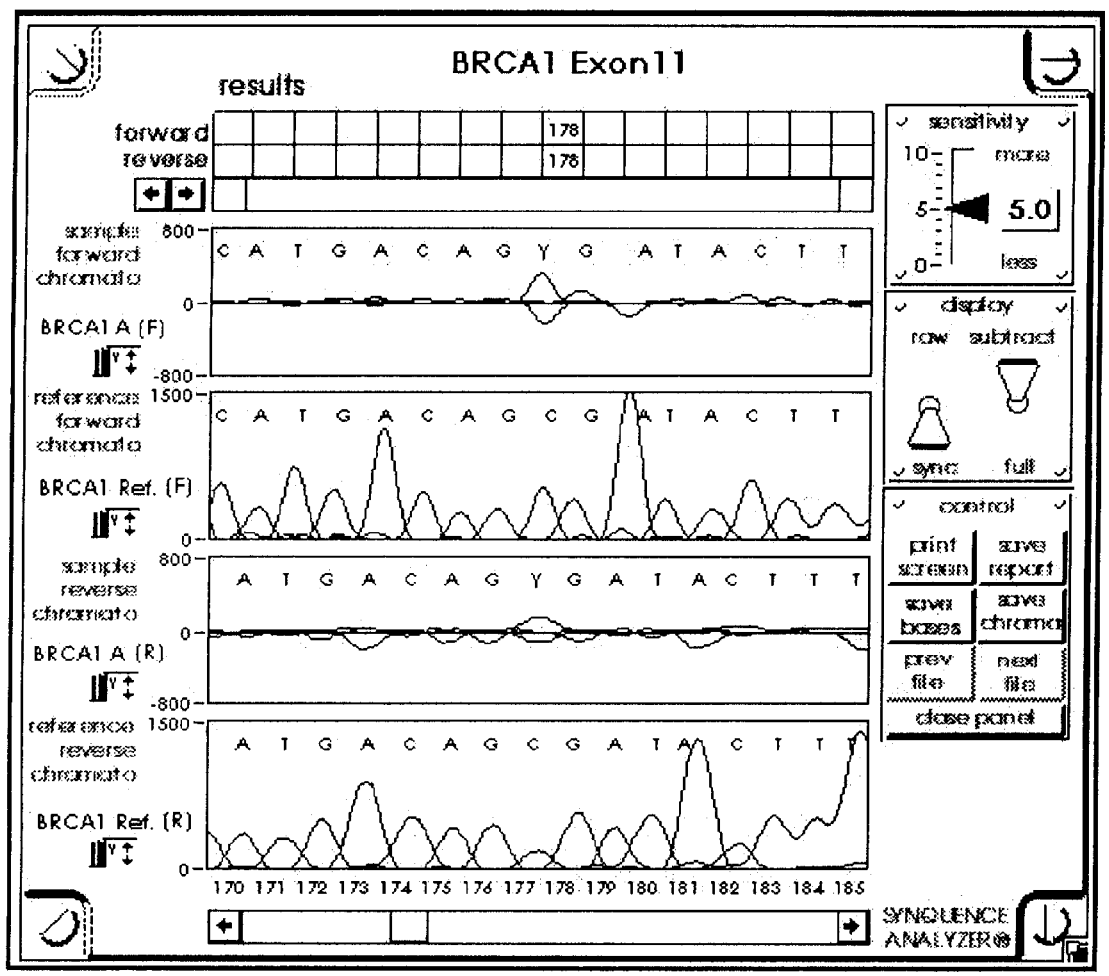

The best mode presently contemplated for carrying out the invention is illustrated in the accompanying drawings, in which:

FIG. 1 is a chromatographic depiction of the analog signal generated from a nucleotide sequencing apparatus of the prior art;

FIG. 2, a flow diagram of steps and operations performed in the preferred embodiment of the invention;

FIG. 3, a view of an initial user interface screen;

FIG. 4, a view of a batch editor user interface screen;

FIG. 5, a view of a batch execution user interface screen;

FIG. 6, a more detailed flow diagram of the Peak Detection and Feature Extraction step of FIG. 2;

FIG. 7, a more detailed flow diagram of the Feasibility Verification step of FIG. 2;

FIG. 8, a more detailed flow diagram of the Synchronization step of FIG. 2;

FIG. 9, a more detailed flow diagram of the Signal Difference Detection and Filtration step of FIG. 2;

FIG. 10, a depiction of a computer display screen showing user interface options and four chromatograms, the peaks of each synchronized to show the same region under analysis; from top to bottom a sample forward chromatogram, a reference forward chromatogram, a sample reverse chromatogram, and a reference reverse chromatogram; and FIG. 11, a computer display screen similar to FIG. 2, only the similarities in the sample chromatogram have been subtracted away.

DETAILED DESCRIPTION OF THE ILLUSTRATED EMBODIMENT

While the invention may be practiced in several different specific embodiments, and such embodiments and their applications will be described separately, all embodiments are directed to or include the step of detecting chromatogram peaks and extracting a feature vector from the peak features, a quantification of peak parameters, which permits either more accurate base calling than has heretofore been possible or automated comparison of two or more chromatograms and individual peaks within those chromatograms which has not heretofore been possible. All embodiments entail obtaining a digital data file derived from an analog signal representative of the emission spectra of an excited fluorophore labeled nucleotide polymer obtained during nucleotide investigations such as sequencing runs performed in conjunction with polyacrylamide gel or capillary electophoresis.

Processes, including processes such as nucleotide sequencing and others, are known which result in the collection of emission spectra data of fluorophore labeled nucleotide polymers of varying length as they undergo separation according to length. As discussed in the background, some of these employ gel electrophoresis and some capillary electrophoresis to achieve separation of the fragments over time by virtue of the fragment length dependent differences in migration time through the separation means. As the tagged nucleotide polymers are separated and cross the detector array or "finish line" so to speak, a time dependent signal is generated, and eventually converted to a digital format. An example of a nonsequencing process is the microsatellite amplification and detection process. The invention is equally applicable to all such methods employing fluorphore labeled nucleotide polymers which result in a data file representative of their emission spectra generated over time as they undergo separation according to length.

Automated sequencing machines such as the ABI models are capable of generating large data files and are commercially available and well known to those skilled in the art. The initial data files employed by the invention can be obtained by instruments which provide an optical system which focuses a beam of electromagnetic energy onto the gel containing multiple lanes of fluorophore labeled nucleotide polymer fragments. In usual practice four different fluorophores are employed and all four sequencing reaction products are run in one lane. The fluorescence emitted as a result of the stimulation by the electromagnetic beam is detected in order to provide an electrical measurement of the fluroescent emissions over time and at selected wavelengths. The data thus obtained is transmitted to a data file. Data files representing the analog data measured are then interpreted through the use of a computer program to convert the data to a form representing a chromatogram. An example of one such conversion program is the Applied Biosystems, Inc. software for use on a Macintosh® platform available from Applied Biosystems, Inc., Foster City, Calif. A chromatogram is a graphical representation of the fluorescence detected by the sequencer and graphically shows peaks indicating emission detection.

A plotted chromatogram as obtained by the Applied Biosystems, Inc. sequencer and conversion software is shown in FIG. 1. Signal peaks such as those indicated by reference numbers 30, 31, 32, and 33 indicate detected ends of nucluotide polymer fragments. These peaks also indicate the bases forming the ends of the nucleotide fragments. Where all four sequencing reaction products are run in one lane, the chromatogram produces color traces. By convention, green is used to represent A peaks, blue is used to represent C peaks, black is used to represent G peaks, and red is used to represent T peaks. Of course, other colors could be used. In FIG. 1, peak 30 would be in red showing a T, peak 31 would be in blue showing a C, peak 32 would be in black showing a G, and peak 33 would be in green showing an A. The chromatogram will generally label the peaks with the appropriate letter above the peak, as shown. Where the software cannot determine the base, as at area 34, the letter N, shown at 35, will be inserted on the chromatogram.

Data Importation

As shown by the flow chart of FIG. 2, the first step in the process of the invention is to obtain the digital data files to be labeled, evaluated, or otherwise worked with. These files will generally be the standard chromatogram data files produced by the various commercial sequencing machines as described above, the data representing chromatograms such as shown in FIG. 1. As indicated, any data file containing chromatogram type data may be evaluated using the method of the invention.

Once the data file or files to be evaluated have been obtained, the data from the files is imported into the computer used to perform certain of the steps of the invention. The data may be imported into the computer via a diskette, CDrom, or other media containing the data, or by direct link with another computer where the data is stored such as through a local area network, direct connection, ethernet, internet, etc.

An importation interface may be provided having several user actuated options such as: the selection of one or more data files into a data batch to undergo analysis, and if at least two data files are imported, the option to select one data file as the reference and another as a sample for comparison with the reference. Preferably, the computer is configured to permit importation of multiple data files by means of the import function while the user interface provides the user with the ability to select or deselect individual data files for inclusion in a batch file.

An example of an initial user interface screen is shown in FIG. 3. As depicted, pull down menus such as a File menu, Edit menu, Batch menu, and a Help menu can be made accessible to the user. Options available to the user under these menus may be comparable to those of such widely known programs such as Windows® 3.1 or Windows 95®, Macintosh OS®, and Windows NT® interfaces.

From the main menu screen, entry can be gained to a batch editor screen. An example of a Batch Editor user interface screen is shown in FIG. 4. This screen of the importation interface provides the user with the options to sort imported files, show the date, select imported files for inclusion in a batch file, "Add to Batch" option, or "Remove" if after addition the user desires to deselect the data file, select a reference data file, "Make Reference", and "Cancel" or "OK" the user selected "Batch Contents".

The next step, step 3, depicted in the flow diagram of FIG. 2 is analysis. After the user has selected the desired data and sample, if desired, and selects "OK" to start the analysis, a "Batch Execution" interface screen pops up. This screen shows the progress of the analysis with a bar indicator 40 and provides the user with an "Abort" option. If allowed to proceed without interruption the analysis steps take place automatically without the need for user input. If a single forward chromatogram was selected for analysis, the data file passes directly to a "Peak Detection and Feature Extraction" step. If one or more data files are selected for comparison with a reference, a "Feasibility Verification" step takes place first, followed by a "Peak Detection and Feature Extraction" step, a "Synchronization" step and a "Signal Difference" detection step. Upon completion of the analysis an "Interactive Analysis Interface" screen pops up. This interface provides the user with the option to view chromatograms, perform "Polymorphism Analysis", save synchronized chromatograms and new base calls in a custom file, obtain a subtracted view of a sample and the reference chromatograms with all similarities removed, adjust the sensitivity of the subtraction parameters, or obtain a side by side comparison view of a pair of either synchronized sample and reference chromatograms or a pair of unsynchronized sample and reference chromatograms.

The interface also preferably provides the user the option to export a nucleotide sequence, export an analysis picture, and save "new" base calls performed by the software of the invention inside an existing chromatogram file.

Peak Detection And Feature Extraction

As mentioned, a common step to all of the embodiments of the invention is the extraction of a vector from each peak's features. This will usually be done in a "Peak Detection And Feature Extraction" step as diagramtically depicted in FIG. 6. The extracted features currently contemplated as the best for employment with the analytical steps of the invention include peak spacing, amplitude (height), area under the peak, presence of a secondary peak, and second time domain derivative of peak evolution and devolution. As an optional first substep, prior to feature extraction, chromatogram signals are corrected for certain distortions such as peak clipping and contextual influences. This operation is equivalent to noise removal as performed in speech recognition software programs. As a further option and second substep, the peak shape can be enhanced using the extracted peak feature known as the second time domain derivative of the chromatogram signals (a derivative of the time of evolution and devolution of the peak) to improve peak separation. As a third substep, peaks are then detected on the corrected, if opted for, chromatogram signals. This detection substep is somewhat analogous to phoneme or phone segmentation in speech recognition software programs.

The fifth substep shown on FIG. 5, is the extraction of a vector for each peak detected. Optimally, five features are extracted, and the features extracted together are used to calculate or form a vector which quantifies peak parameters such as peak spacing, height (of the four dye signals in the chromatogram), area under the peak, presence of secondary peaks, evolution and devolution of the peak over time, or, even more preferably the second time domain derivative of peak evolution and devolution. Peak spacing after correction, enhancement, and alignment has been found of great utility in performing chromatogram comparison analysis. This substep is equivalent to calculating MFCC spectral features and signal energy in speech recognition software but the scope is only the segmented phone, not a fixed loms analysis as used for HMMs in speech recognition.

The sixth and final substep of Peak Detection and Feature Extraction as shown in FIG. 6 is insertion and deletion of peaks from the chromatogram in order to satisfy peak spacing continuity criteria. This operation is ruled by local stimulations of the average peak spacing. This substep is equivalent to phoneme insertion and removal in speech recognition technologies. In speech recognition technology, removal and insertion is based on phoneme duration criteria and local speech rate estimations. The automated analysis and quantification of peak parameters into feature vectors is a highly useful tool with two applications of primary interest being base calling and comparing one sample to another, such as a sample to a reference. Construction of the programming to perform the multistep process indicated above is well within the skill of a programmer familiar with speech recognition technology.

For optimal base calling, an identification of the base is derived preferably from at least three feature vectors, preferably spacing, height, and area under the peak, presence of other peaks, and second time domain derivative of peak chromatogram signals, preferably using the corrected and enhanced peaks and the corrected chromatograms according the sixth substep above. Of course, the base call is made not solely with the extracted feature vectors, but also in conjunction with the standard base calling algorithm which relates the emission spectrum of a fluorophore tag to the purine or pyrimidine base to which it is tagged and the relative position of the base in the sequence of the nucleotide polymer based on its relative time of migration past the electromagnetic wave source and detector array (gel electrophoresis) or CCD camera array as the case may be (capillary electophoresis).

The calling is preferably done using a vector extracted from all five peak features. One beneficial result of quantifying peak parameters in a vector is that truth values or scores can be calculated from the vector and assigned to the base call wherein the degree of certainty of the validity of the call can be assigned to the call rather than the, binary, yes or no, determination made by prior art base callers. In the best mode currently contemplated, a two fold base call is made. In other words, the most likely and the second most likely bases are identified. The method employed to make this multifold base call is similar to the method employed in speech recognition technology for calculating MFCC spectral features and signal energy, except the scope is only the segmented phone, not a fixed 10 ms analysis as used for HMMS.

It is difficult, if not impossible, to achieve 100% correct "recognition" of all the bases. The invention entirely avoids a yes or no "recognition" of the bases, but instead "identifies", or, perhaps more aptly, "labels", a peak with its most probable and second most probable base and adds those labels to the feature vector for comparison analysis. A user interface can provide for the calls, which can be tentative, to be reported to the user on a computer screen or "exported" as ASCII text for use in comparison feasibility analysis as desired.

Comparison of Chromatograms From A Sample And A Reference

Perhaps the most important solution provided by the invention is to the problem of comparing two or more data files containing chromatograms from nucleotide sequencing and the determination of polymorphisms, otherwise ambiguous base calls, and distinguishing between the two. The multi-step process comprising the Peak Detection and Feature Extraction step was discussed above. Below is an account of how this Peak Detection and Extraction Step in conjunction with three additional steps provides a solution to the aforementioned problem. The first of the three additional steps is a Feasibility Verification Step, or, "gross" alignment step. This is followed by the Peak Detection and Extraction step, the Synchronization, or "fine" alignment step, and finally a Signal Difference Detection and Filtering Step.

Feasibility Verification

"Feasibility Verification" is understood to mean herein a determination of gross compatibility between a sample and a reference as determined by a comparison of base sequence. Base calls can be made from feature vectors according to the invention or from prior art base callers. As shown in FIG. 7, original base calls, in other words, the ASCII files denoting the base called base sequence (e.g., A-N-A-A-C-G-T-T-A-) are compared between a sample and a reference by matching sets, preferably, ten base calls, from the sample to the reference. Comparison continues in set by set increments and is repeated until gross alignment is achieved or the sample is rejected to nonalignment. A binary, yes or no, match decision is made.

The process is repeated for each sample within a batch. If gross alignment is possible for all samples within the batch, then the batch is valid for proceeding with comparison to the reference. With the batch so verified, analysis proceeds to the synchronization step. Otherwise data files within the batch which are not verified are signaled to the suer so the user may deselect or remove them from the batch. The gross alignment suggested in this step is used as a starting point for a second gross alignment and a fine alignment in the "Synchronization" step which follows.

Synchronization

Comparison of two chromatograms to detect differences between them is the present best application of the invention and is shown in FIG. 8. Although Peak Extraction and Detection was considered first in this detailed description of the invention, in this preferred application of the invention, two data files are first analyzed for the feasibility of comparison, the peak detection and extraction is performed, and then the chromatograms are synchronized based on vectors derived from preferably corrected and enhanced peaks.

For each sample/reference pair the gross mapping or alignment function is recalculated preferably using subsets of 10 peaks, and using extracted feature vectors. The ASCII base call file is not used. In comparing extracted feature vectors, fuzzy truth values or scores are calculated from comparison of the vectors of the sample to the vectors of the reference. A binary, yes or no decision, is not used. Then a further alignment, designated as "fine alignment" takes place consisting of "mapping" each possible peak triplet from sample to reference. Using the peak triplets as a decision unit is somewhat comparable to the use of triphone decision units used in HMM (hidden markov models) in speech recognition techniques. Of course, a triplet naturally lends itself to a decision unit for taking into account contextual influences and this use makes possible the invention's correction of the ambiguities imposed by contextual influences. The fuzzy logic score makes alignment possible in regions of the sequence where a classical base call comparison (yes or no) would not be able to generate a correct fine alignment.

Peak pairs are selected from the fine alignment which have yielded a sufficient score and a chromatogram mapping function is calculated from those pairs. This operation is somewhat analogous to speech recognition mapping function calculations using the dynamic time warping "DTW" algorithm. The mapping function is filtered in order to eliminate possible discontinuities. Such filtering is allowed because the gel migration speed is locally constant. The sample chromatogram is recalculated using the mapping function. Because the gel migration speed is locally constant, the mapping function can be interpolated in order to find the equivalent data point in the sample chromatogram for each data point in the reference chromatogram.

By these substeps, the x-axis is stretched or compressed to conform to the reference. These Synchronization "decisions" occur on a very localized scale. Consequently, the decisions do not change the basic shape, intensity, or position of the data peak and, thus, data integrity is preserved and only real differences in the data are compared and quantified. The aforementioned substeps of syncronization correct for the stretching and compressing of the investigation data that occurs due to stochastic events in, e.g., gel electrophoresis (degradation, nonuniformity of gels, temperature and electric current variations, etc.). This step can be applied to syncronize the chromatograms of a forward sequencing sample to a forward reference or chromatograms of a reverse sample to a corresponding reverse reference, in other words, between any two chromatograms at least initially determined to represent the identical, or at least nearly the same sequence. Because the chromatogram peaks of forward and reverse sequencing investigations represent base sequences that are complimentary and not simply in reverse order, syncronization, and consequently peak by peak comparision cannot take place between a forward and reverse sample. However, an algorithm for comparing the bases of forward and reverse runs is done, preferably using the "tentative" base calls generated by the basecaller of the invention.

Signal Difference Detection And Filtration Step

Details of the Signal Difference Detection and Filtration step are shown in FIG. 9. Any signal difference between sample and reference is considered a potential polymorphic locus, the difference being based upon comparison of the the vector derived from the extracted features of the two peaks being compared and not ASCII text base calls. Heterozygous polymorphic conditions are suggested by a signal difference at a specific locus (the peak number on the chromatogram), the difference being more particularly defined as a decrease in signal intensity of one base as indicated by its vector and the presence of a signal from a different base at the same locus, i.e., its vector. Homozygous polymorphisms are indicated by the absence of signal in a predicted base and the presence of signal in a different base at a locus. Polymorphisms comprised of small insertions and deletions can also be detected by superimposing a pair of chromatograms from both alleles on one another and observing a frameshift. The nonmatching bases associated with the frameshift (insertion or deletion) between the two chromatograms are ignored because the previous feasibility and synchronization steps have determined the chromatograms are comparable. Miscalled N bases are also consequently ignored.

When several data files are selected into the batch file and analysis begins, in a preferred embodiment, the computer is configured to process the first forward sample and a single forward reference and compare the two by a feasibility protocol. If the sample passes, i.e., the feasibility of comparison is "verified", then sample and reference proceed to the next steps: Peak Detection and Extraction; Synchronization; and Signal Difference Detection (which preferably includes polymorphism analysis). After these steps, the results are preferably written to the, e.g., hard drive memory after which the next forward sample runs through the same steps, and then the next forward sample and so on until all the forward are finished for the first batch file. Normally, the computer will be configured to compare one or more reverse samples, if imported and selected, to a single reverse reference sample just as with the forward sample analysis, i.e., one at a time, then store the result, then process the next sample, but only after all the forward sample or samples in the batch are processed.

Interactive Analysis Interface

Preferably, an "interactive analysis interface", an embodiment of which is shown in FIG. 10 provides the user many options. In this particular embodiment, the interface view screen is entitled SYN-QUENCE Mutation Panels. For polymorphism analysis and detection, preferably a comparison is made among four chromatograms; the sample forward chromatogram; the reference forward chromatogram; the sample reverse chromatogram; and the reference reverse chromatogram. In FIG. 10, the aligned portions of four such chromatograms are depicted from top to bottom in the aforementioned order; the sample forward chromatogram; the reference forward chromatogram; the sample reverse chromatogram; and the reference reverse chromatogram, and named to the left side of the screen. A "detected differences display", the sixteen column, two rows of squares, extending horizontally across the top of FIG. 2, is where detected differences are reported in this particular embodiment of a user interface. This display bears the title "results" in this embodiment. Each box is hypertext. In FIG. 2, a difference is signaled at position 178. The called bases appear across the top of each chromatogram and the apparent sequence number across the bottom. A scroll bar at the bottom of the screen allows the user to scroll right (higher in the sequence) or left (lower in sequence). In the upper, right hand corner is a sensitivity control, entitled "sensitivity" on the view screen that provides the user the ability to click and drag an indicator up and down a scale from 0 to 10. At higher sensitivity setting, smaller difference will be detected and displayed in the "results" display and vice versa. This can be configured to work in real time without the requirement of reanalyzing the data. Thus, the user may quickly evaluate and re-evaluate a chromatogram. A "chromatogram display control" entitled on the view screen as simply "display" appears below the sensitivity control providing the user the option to view the displayed chromatograms in synchronized or unsynchronized or "raw" mode, in full view, or in a "subtracted" view where all the similarities are subtracted and only the differences in the chromatograms remain. Below the "chromatogram display control" is another control menu, entitled "control" providing the user the option to print screen, save report, save cases, save chromatograms, view the previous or next file, or close the panel.

FIG. 10 is a full, synchronized view of the displayed chromatograms while FIG. 11 is a subtracted view of the same portion of the same chromatograms. In the subtracted view, the signal differences between sample forward and reverse chromatograms at position 1878 is readily appreciated.

It is further contemplated by the invention to provide an apparatus which generates or imports a digital data file representative of fluorophore emissions detected during observation of fluorophore labeled nucleotide polymers, extracts feature vectors, and, optionally calls bases indicated by the feature vectors, and, further optionally, analyzes and compares chromatographicly two or more data files which may be filtered, corrected, and enhanced, and synchronized according to the steps above discussed.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

What is claimed is:

1. An automated method for comparing a first DNA sequence and a second DNA sequence wherein the features of one or more peaks from each digital data file that is representative of a chromatogram generated during DNA sequencing are quantified and compared, comprising the steps of:
   a) Obtaining two digital data files each containing at least one peak;
   b) Importing said data files into the memory of a digital computer device;
   c) For each peak of each data file, extracting a feature vectors wherein three or more peak parameters are quantified;
   d) synchronizing said digital data files to be compared based on the feature vectors extracted for each data file;
   e) comparing the feature vectors of corresponding peaks in the synchronized data files; and
   f) detecting differences in the feature vectors.

2. A method according to claim 1 further comprising the steps of:
   Allowing a user to designate one of said digital data files as a reference and the remaining file or files as samples.

3. A method according to claim 2 wherein the differences are assigned truth values.

4. A digital computer device for use with at least two digital data files representing chromatograms from a first DNA sequence and a second DNA sequence generated during DNA sequencing, each data file containing at least one peak, said computer configured to:
   a) import said digital data files into the memory of the digital computer device;
   b) calculate a vector for each peak which quantifies three or more peak parameters;
   c) synchronize said digital data files to be compared based on the feature vectors extracted for each data file;
   d) compare the feature vectors of corresponding peaks in the synchronized data files; and
   e) detect differences in the feature vectors.

5. A device according to claim 4 further configured to:
   allow a user to designate one or more imported digital data files as samples and another digital data file as a reference.

6. A device according to claim 4, wherein the vector is calculated upon the extracted features of peak height, second time domain derivative, and peak shape.

7. A method according to claim 1 wherein one feature vector is extracted selected from the group of features including peak shape, area under the peak, and the second time domain derivative of the peak.

8. A method according to claim 1 wherein the extracted feature vectors are derived from peak height, second time domain derivative, and peak shape.

9. A method according to claim 1 including a step of calling a base from said feature vector.

10. A method according to claim 1 including detecting the at least one peak, further comprising the step of correcting the peak information prior to detecting the peak.

11. A method according to claim 1 including detecting the at least one peak, further comprising the step of enhancing the peak information prior to detecting the peak.

12. A method according to claim 1 including detecting the at least one peak, further comprising the steps of correcting and enhancing the peak information prior to detecting the peak.

13. A method according to claim 2, wherein the two or more digital data files include data files from differing runs of the same nucleotide polymers.

14. A method according to claim 2, wherein the two or more digital data files include data files of different nucleotide polymers.

* * * * *